(12) United States Patent
Tompkins (10) Patent No.: US 10,900,004 B2
(45) Date of Patent: Jan. 26, 2021

(54) OPEN LOOP ADDITIVE MATERIAL PROCESS AND SYSTEM FOR CREATING A HUMAN-HABITABLE ENVIRONMENT

(71) Applicant: Daniel Tompkins, Tampa, FL (US)

(72) Inventor: Daniel Tompkins, Tampa, FL (US)

(73) Assignee: DIY Service LLC, Tampa, FL (US)

( * ) Notice: Subject to any disclaimer, the term of this patent is extended or adjusted under 35 U.S.C. 154(b) by 150 days.

(21) Appl. No.: 16/220,935

(22) Filed: Dec. 14, 2018

(65) Prior Publication Data

US 2019/0185797 A1 Jun. 20, 2019

Related U.S. Application Data

(60) Provisional application No. 62/598,470, filed on Dec. 14, 2017.

(51) Int. Cl.

| | |
|---|---|
| *C12M 1/107* | (2006.01) |
| *C12M 1/00* | (2006.01) |
| *C12M 1/26* | (2006.01) |
| *B33Y 70/00* | (2020.01) |
| *B29C 64/357* | (2017.01) |
| *B33Y 10/00* | (2015.01) |

(Continued)

(52) U.S. Cl.

CPC .......... *C12M 21/04* (2013.01); *B29C 64/357* (2017.08); *B33Y 70/00* (2014.12); *C12M 21/02* (2013.01); *C12M 33/12* (2013.01); *C12M 47/06* (2013.01); *B29C 64/118* (2017.08); *B29K 2067/04* (2013.01); *B29K 2995/006* (2013.01); *B33Y 10/00* (2014.12); *B33Y 40/00* (2014.12)

(58) Field of Classification Search
None
See application file for complete search history.

(56) References Cited

U.S. PATENT DOCUMENTS

2017/0327704 A1 11/2017 Sacripante et al.

FOREIGN PATENT DOCUMENTS

WO 2011035166 A1 3/2011

OTHER PUBLICATIONS

Kucherov et al., Angew. Chem. 56: 15931-15935 (2017).*

(Continued)

*Primary Examiner* — Erin M. Bowers
(74) *Attorney, Agent, or Firm* — Smith & Hopen, P.A.; Paul Murty (57) ABSTRACT

Methods for producing hydrocarbon-based polymers and hydrocarbon-based polymeric structures that are capable of removing carbon dioxide from an ambient environment to produce breathable oxygen. The methods produce enclosed, solar-exposed polymeric structures capable of expanding in area through the reuse of at least a portion of the hydrocarbon-based polymers. As such, the method produces self-sustaining polymeric/hydrocarbon-based structures capable of in-situ resource harvesting and reuse to create a sustainable, habitable area. The methods can be used to create a habitable environment in otherwise harsh conditions, such as those associated with high concentrations of carbon dioxide and low pressure, without the need to use external, non-renewable resources, and instead using renewable, in-situ resources to improve the viability of habitation within the environment of the manufactured three-dimensional structures.

10 Claims, 6 Drawing Sheets

(51) Int. Cl.
*B33Y 40/00* (2020.01)
*B29C 64/118* (2017.01)
*B29K 67/00* (2006.01)

(56) References Cited

OTHER PUBLICATIONS

International Preliminary Report on Patentability for PCT/US18/65772 (International Filing Date: Dec. 14, 2018) with a priority dated Dec. 14, 2017; Applicant: DIY Service LLC
Kucherov et al., Three-Dimensional Printing with Biomass-Derived PEF for Carbon-Neutral Manufacturing. Agnew. Chem. Int. Ed. 2017. vol. 56: 15931-15935.
Murukesan et al, Pressurized Martian-Like Pure CO2 Atmosphere Supports Strong Growth of Cyanobacteria, and Causes Significant Changes in their Metabolism. Orig. Life Evol. Biosph. 2016. vol. 46: 119-131.
Lingampalli et al., Recent Progress in the Phtotocatalytic Reduction of Carbon Dioxide. ACS Omega. 2017. vol. 2: 2740-2748.
Dexter et al, The state of autotrophic ethanol production in Cyanobacteria. Journal of Applied Microbiology. 2015. vol. 119: 11-24.
Gurudayal et al., Efficient solar-driven electrochemical CO2 reduction to hydrocarbons and oxygenates. Energy Environ. Sci. 2017. vol. 10: 2222-2230.
Markou et al, Microalgal carbohydrates: an overview of the factors influencing carbohydrates production, and of main bioconversion technologies for production of biofuels. Appl. Microbiol. Biotechnol. 2012. vol. 96 (No. 3): 631-645.
Dashtban et al., Production of Furfural: Overview and Challenges. Journal of Science & Technology for Forest Products and Processes. 2012. vol. 2 (No. 4): 44-53.
Van Der Hoeven. More biobased plastics for bottles: DuPont accounces PTF. Bio Based Press. Feb. 2, 2016. [online]. Date Accessed: Mar. 18, 2019. https://www.biobasedpress.eu/2016/02/more-biobased-plastics-for-bottles-dupont-announces-ptf/.
Dupont. Sustainable Plastics. [online]. Date Accessed: Mar. 18, 2019. http://www.dupont.com/products-and-services/plastics-polymers-resins/bio-based-polymers/articles/renewable-biopolymers.html.
Nestle. Danone and Nestle Waters Launch NaturALL Bottle Alliance with California Startup to Develop 100% Bio-Based Bottles. Mar. 2, 2017. [online]. Date Accessed: Mar. 18, 2019. https://www.nestleusa.com/media/pressreleases/nestle-waters-launch-alliance-naturall-bio-based-bottles.
Synvina: functional systainable Bioplastics. PEF Game Changing Plastic. [online]. Date Accessed Mar. 18, 2019. https://www.synvina.com/products/pef/.
Pellicori. Coatings Used in Space: Requirements and Solutions. Materion Technical Paper: Materion Coating Materials News: 1-6. [online]. https://materion.com/-/media/files/advanced-materials-group/ac/ac-newsletter-article-pdfs/coatings-used-in-space_technical-paper.pdf?a=en&hash=14D82EF63631DC7C39D2EAD25FECDE66AD5E3BB0.
Gibson et al. Development of NASA's Small Fission Power System for Science and Human Exploration. American Institute of Aeronautics and Astronautics: 1-10. [online]. Date Accessed: Mar. 18, 2019 https://ntrs.nasa.gov/archive/nasa/casi.ntrs.nasa.gov/20140017750.pdf.
Maverickmpls. Zen Windmill Powered Water Pump. Thingiverse. Aug. 1, 2015. [online]. Date Accessed: Mar. 18, 2019. https://www.thingiverse.com/thing:950660.
Holstein-Rathlou et al. Wind Turbine Power Production Under Current Martian Atmospheric Conditions. Mars Workshop on Amazonian Climate (LPI Contrib. No. 2086). 2018. [online]. Date Accessed Mar. 18, 2019. https://www.hou.usra.edu/meetings/amazonian2018/pdf/4004.pdf.
Wheeler. Agriculture for Space: People and Places Paving the Way. Open Agriculture. 2017. vol. 2: 14-32.
Verseux et al., Sustainable life support on Mars—the potential roles of cyanobacteria. International Journal of Astrobiology. 2016. vol. 15 (No. 1): 65-92.
Menezes et al., Towards synthetic biological approaches to resource utilization on space missions. J.R. Soc. Interface. 2014. vol. 12: 1-20.
International Search Report and Written Opinion for PCT/US18/65772 (International Filing Date: Dec. 14, 2018) with a dated Feb. 19, 2019; Applicant: DIY Service LLC.

\* cited by examiner

OPEN LOOP ADDITIVE MATERIAL PROCESS AND SYSTEM FOR CREATING A HUMAN-HABITABLE ENVIRONMENT

CROSS-REFERENCE TO RELATED APPLICATIONS

This nonprovisional application is a continuation of and claims priority to provisional application No. 62/598,470, entitled "Open Loop Additive Material Process," filed Dec. 14, 2017 by the same inventor.

BACKGROUND OF THE INVENTION

1. Field of the Invention

This invention relates, generally, to self-sustaining additive manufacturing processes in which resources can be recycled and reused throughout an additive manufacturing project. More specifically, it relates to in-situ resource utilization and resource recycling in an open-loop, such that local resources can be utilized in creating structures and new structure expands local material production rate.

2. Brief Description of the Prior Art

As technology advances and as resources on Earth become more limited, the needs for renewable resources and for renewable sources of energy become increasingly important for the long-term survival of Earth's inhabitants. In addition, scientific consensus shows that emissions from human-made technology, as well as naturally-occurring events, has created an abundance of carbon dioxide in Earth's atmosphere, which is linked to climate change and catastrophic weather events. Attempts have been made to solve the aforementioned issues, such as by turning to renewable energy derived from wind, waves, and sunlight; moreover, attempts have been made to reduce or alter the materials used in industrial processes, as well as plant photosynthetic sources to remove carbon dioxide from the atmosphere. Regardless of the efforts thus far, the issues of high emissions, high fossil fuel usage, and high concentrations of carbon dioxide (and other gases) remain detrimental to the long-term survival of Earth's inhabitants.

In part due to these issues, and in part due to scientific curiosity and the desire for more knowledge of Earth's surroundings, the viability of settlement in extraterrestrial environments continues to be explored by both public and private organizations. One environment in particular that remains near the top of the list of potentially-viable settlement locations is that of Mars, Earth's typically-second-closest neighboring planet, as evidenced by NASA's Curiosity rover and InSight lander currently-active on the Martian surface. This is, in part, due to Mars's atmosphere, the likely presence of water within the Martian ground surface, and Mars's ice caps. However, aspects of Martian conditions make the possibility of settlement difficult without the help of technological innovations—namely, the Martian atmosphere contains vast amounts of carbon dioxide; Mars has a drastically lower atmospheric pressure than that of Earth; and Mars has an ambient temperature much lower than that of Earth. Each of these characteristics of Mars make the possibility of successful settlement on the planet all but impossible without the aid of technological life support systems. Moreover, the long-term success of a settlement on an extraterrestrial body depends on the use of resources natural to the extraterrestrial body, or renewable resources that can be transported to the extraterrestrial body for use and reuse; without such renewable/natural resources, settlements would require replenishments from external sources, which is not viable for a long-term settlement.

One resource that is currently being used on Earth to decrease the reliance on plastics and to decrease energy usage during additive manufacturing processes is algae-based filament. By introducing algae into traditional filament, additive manufacturing structures can be created at lower temperatures, because there is a decreased need to melt the filament that is traditionally used in additive manufacturing. Moreover, algae decreases the amount of plastic used in an additive manufacturing project, thereby using a more sustainable resource than the less-sustainable plastic filaments that are traditionally used. While algae-based filaments are known in the art, there remains a need for reusable filament components, which can help create an even more sustainable structure; an object of this invention, as discussed in greater detail below, is to utilize such algae-based filaments in reusable and recyclable ways.

With the above discussion in mind, photosynthetic organisms, such as algae and algae-based materials, can play a role in contributing to the habitability of an environment, such as an extraterrestrial body. As discussed above, Mars provides a potential settlement location for human exploration outside of Earth; however, also as discussed above, the harsh conditions on Mars make settlement all-but-impossible without the aid of technological innovations. However, photosynthetic organisms can be used in environments with greater-than-desired concentrations of carbon dioxide to remove excess carbon dioxide from the environment, creating breathable oxygen as a byproduct of the photosynthetic reaction. As such, it has been theorized that photosynthetic organisms, such as algae, can be employed in Martian-like atmospheres to create more habitable environments therein.

The low input fertilizer mass needed to support highly functional biological life support schemes supplying food and oxygen were recognized early in space exploration but complex to implement into a fixed closed loop scheme [16]. Constant thermoregulation via radioisotope power systems or fission power systems provides 24-hour heat source that can further utilized and maintain temperatures need for biological systems. The following discussion provides an overview of the relevant existing technologies prior to discussing the present invention in greater detail. [13]

However, simply transporting and/or cultivating photosynthetic organisms on Mars will ultimately contribute little to the overall viability of the planet as a potentially-habitable settlement location for Earth's inhabitants. Moreover, without a sustainable and growing population of photosynthetic organisms on Mars, such a settlement stands little chance at long-term success without the need for continuous refueling missions. Accordingly, what is needed is an in-situ solution to problems associated with limited and/or non-renewable base resources, providing a method for recycling and reusing a portion of the resources, thereby creating an open loop process for use in combination with additive manufacturing. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an in-situ solution for resource replenishment and reuse, and for creating an expandable habitable area through the use of polymeric material including hydrocarbon-based components, is now met by a new, useful, and nonobvious invention.

The novel method includes a step of providing a bioreactor including an aqueous mixture and a concentration of atmospheric gases, with a hydrocarbon fixing, bioactive, or $CO_2$ fixing organism disposed within the aqueous mixture. The bioreactive organism is separated from the aqueous mixture. A first compound is formed by crushing, hydrolyzing, and dehydrating the hydrocarbon-based organism. The first compound is reacted to produce a first set of monomeric units. A second compound is made by fermentation or pyrolysis or hydrothermal pyrolysis of the organism. The first set of monomeric units is reacted with a second set of monomeric units to produce a polymeric compound. The polymeric compound is formed into a resin. The resin is heated and extruded to form a hydrocarbon-based filament for use in generating a three-dimensional structure via an additive manufacturing machine. The atmospheric gases include at least 10% $CO_2$ and less than 3% $O_2$. The bioreactive organism is algae. The biological reactor is operated at a pressure approximately equal to a pressure of an ambient environment surrounding the biological reactor to minimize power requirements and pressure losses due to leaks. The first compound is selected from the group consisting of 5-hydroxymethylfurfural, dimethylfurfural, furan, and p-xylene. The first set of monomeric units is selected from the group consisting of furandicarboxylic acid, succinic acid, itaconic acid, and terephthalic acid, or other dicarboxylic acids or esters or diesters thereof. The second set of monomeric units is selected from the group consisting of ethylene glycol, 1,4-butanediol, 1,3-propanediol, and 1,2-propanediol, or other diols or their mono- or di-esters. At least one dicarboxylic acid, or ester, or diester thereof is polymerized with at least one diol or ester or diester thereof, to produce a polymeric resin. The resin produced from the polymerization comprises a material selected from the group consisting of poly-(butylene-succinate), poly-(butylene-2,5-furanate), poly-(butylene-itaconate), poly-(propylene-succinate), poly-(propylene-2,5-furanate), poly-(propylene-itaconate), poly-ethyleneterephthalate, and mixtures thereof. The three-dimensional structure is selected from the group consisting of translucent films, plates, sheets, panels, other planar structures, and combinations thereof.

Another embodiment of a method of manufacturing a habitable hydrocarbon-based three-dimensional structure includes a step of removing atmospheric gases into a bioreactor disposed within an ambient environment in communication with an atmosphere containing the atmospheric gases. Optionally, gases collected from within human habited facilities or power generating facilities can be used in place of the atmospheric gases. The removed atmospheric gases are reacted with an aqueous mixture including a hydrocarbon-based organism to form a solid biomass. The solid biomass is digested with a solution of α-hydroxysulfonic acid to form sugars selected from the group consisting of pentose sugars, hexose sugars, and mixtures thereof. The sugars are dehydrated to produce 5-hydroxymethylfurfural. The 5-hydroxymethylfurfural is oxidized to produce 2,5-furandicarboxylic acid. The 2,5-furandicarboxylic acid is reacted with monomethyl ethyleneglycol to form poly ethylene furandicarboxylic acid and methanol. The polyethylenefurandicarboxylic acid is extruded to form a three-dimensional structure. The removal of atmospheric gases reduces the concentration of $CO_2$ in the ambient environment, and wherein the reaction in the bioreactor increases the concentration of $O_2$ in the ambient environment. The three-dimensional structure is an inverted-trapezoidal shape, wherein the shorter of the pair of pair of parallel base surfaces of the inverted-trapezoidal shape is disposed on a ground surface in a first configuration. The inverted-trapezoidal three-dimensional structure is rotatable to a second configuration, in which one of the tapered sides of the inverted-trapezoidal shape is disposed on the ground surface. The inverted-trapezoidal three-dimensional structure is rotatable to a third configuration, in which the other of the tapered sides of the inverted-trapezoidal shape is disposed on the ground surface. The area disposed within the bioreactor can be increased by securing the formed three-dimensional structure to the bioreactor, thereby increasing the habitable area within the bioreactor.

Another embodiment of a method of manufacturing a habitable hydrocarbon-based three-dimensional structure in an environment having low pressure and a high concentration of $CO_2$ includes a step of removing atmospheric gases into a bioreactor disposed within an ambient environment in communication with an atmosphere containing the atmospheric gases, wherein the atmospheric gases include at least 10% $CO_2$ and less than 3% $O_2$, and wherein the ambient environment has less than 0.1 atm absolute pressure. The removed atmospheric gases are reacted with an aqueous mixture including a hydrocarbon-based organism to form a solid biomass, wherein the hydrocarbon-based organism is algae, and wherein the reaction with the atmospheric gases reduces the concentration of $CO_2$ in the ambient environment and increases the concentration of $O_2$ in the ambient environment. The solid biomass is crushed, hydrolyzed, and dehydrated to form a first compound, which is reacted to produce a first set of monomeric units. The first set of monomeric units is reacted with a second set of monomeric units to produce a polymeric compound. The polymeric compound is formed into a resin, and the resin is heated and extruded to form a hydrocarbon-based filament for use in generating a three-dimensional structure via an additive manufacturing machine.

An object of the invention is to provide a method of producing, reusing, and recycling photosynthetic-based plastics for use in an expanding area, creating an open loop between the input material, the output product, and subsequent input material for constructing further structures. Another object of the invention is to provide a habitable environment by producing structures made at least in part with photosynthetic substances that can remove carbon dioxide from the ambient environment, thereby producing breathable oxygen as a byproduct. Yet another object of the invention is to provide a method of making a renewable polymeric structure from in situ resources in an Earth environment, or in an extraterrestrial environment, thereby reducing the need to replenish resources after initial stores of resources are expended. As used herein, "extraterrestrial" means any location off-Earth, including man-made structures outside of Earth's atmosphere, as well as planets, asteroids, moons, and other naturally-occurring locations.

In accordance with the identified objects of the invention, the solar powered hydrocarbon fixation within clear plastic combined with the production of more clear plastic enables many benefits to sustaining life in space including reduction in mass to send to space to provide net oxygen production, food growing area, radiation protection, passive water extraction, rocket fuel production ($O_2$, $H_2$, $CH_4$), megastructure, in efforts to sustain life with negligible resources.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes methods for producing hydrocarbon-based polymers and hydrocarbon-based polymeric structures that are capable of housing organisms for the removal of carbon dioxide from an ambient environment to produce breathable oxygen. Moreover, the present invention includes enclosed, solar-exposed polymeric structures capable of expanding in area through the reuse of at least a portion of the hydrocarbon-based polymers produced therein. As alluded to and discussed in the sections above, objects of the present invention are to produce self-sustaining polymeric/hydrocarbon-based structures capable of in-situ resource harvesting and reuse to create a sustainable, habitable area. By incorporating generic biomass carbon fixation with manufacturing and a known net carbon fixation into plastic and oxygen release, plastic manufacturing provides a certain direction without biological complications. Also accomplished is increasing usable structure and solar capturing area for an increased rate of $O_2$ production.

The use of hydrocarbon-based-based filament for use in additive manufacturing has been disclosed in the prior art. For example, Kucherov teaches a method of three-dimensional printing using biomass-derived polymers for the purpose of manufacturing carbon-neutral structures. [1] The Kucherov article discusses the dangers of over-reliance on non-renewable natural resources that produce carbon dioxide and other gases. According to the article, additive manufacturing provides virtually waste-free manufacturing methods, especially in comparison to traditional manufacturing methods. However, in an effort to improve upon the typical polymers that are used as filament in additive manufacturing systems, Kucherov proposes the use of poly(ethylene-2,5-furandicarboxylate), otherwise known as PEF, which is a biomass-derived polymer that is capable for use in additive manufacturing systems. Moreover, Kucherov teaches that it is possible to recycle and reuse objects printed with PEF by melting the objects, converting the melted material into a filament, and using the filament in an additional additive manufacturing process. Importantly, such recycling practices can contribute to sustainable printing practices, in which printed materials can form the basis of future printed objects. US Publication Number 2017/0327704 to Sacripante also teaches a hydrocarbon-based resin for use in additive manufacturing in an attempt to provide a sustainable material alternative to non-renewable resources used in current manufacturing processes. However, neither Kucherov nor Sacripante teaches the use of gases from a high $CO_2$/low $O_2$ ambient atmosphere or from the waste gases of a habitable facility of support facility, the harvesting of a portion of the PEF used to print an object, the mixing of PEF with other materials (such as minerals or other hydrocarbon-based substances), or the expansion of an area including PEF-printed materials to expand the production of PEF.

Moreover, the need to develop and utilize bio-regenerative systems, particularly for extraterrestrial environments, is discussed in Murukesan, which teaches that cellular growth is possible in high-carbon dioxide and low-pressure conditions, such as those that exist on Mars. [2] Murukesan teaches the use of cyanobacteria, which is a prokaryotic bacterial organism, to remove carbon dioxide from the environment and produce breathable oxygen. According to Murukesan, an important consideration is how to shield the cyanobacteria from hard cosmic radiation, such as that experienced on the Martian surface. Expanding upon such carbon dioxide removal system, Lingampalli teaches the reduction of atmospheric carbon dioxide using photosynthetic agents, which would be necessary in the settlement and long-term success and viability of an environment in an extraterrestrial location, such as Mars. [3] Moreover, Dexter further explores the use of cyanobacteria to produce ethanol as an alternative fuel source that would also function as a carbon dioxide removal system. [4] However, similar to Kucherov and Sacripante above, neither Murukesan, Lingampalli, nor Dexter teaches the harvesting, recycling, and expansion of structures or area needed to create truly sustainable structures from hydrocarbon-based materials.

Gurudayal further teaches solar-driven carbon dioxide reduction methods used to provide alternative energy sources, thereby creating more sustainable energy sources. [5] In the Gurudayal article, a copper-based cathode is used in an electrolysis cell to produce hydrocarbons in a solar-assisted method. The results described in the Gurudayal article suggest that efficient carbon dioxide reduction is possible; however, the article is limited to cathode-anode electrochemical reactions to reduce carbon dioxide, and does not touch on the harvesting, recycling, and expansion needed to create truly sustainable structures from hydrocarbon-based materials. Markou also teaches the use of algae as a food source and fuel source, further explaining how hydrocarbon-based agents can be used to provide both food and fuel for a potential settlement (or as alternatives to currently-used resources on Earth). [6]

Dashtban teaches the production and use of furfural from biomass. [7] As those of ordinary skill in the art would recognize, and as explained in the Dashtban article, furfural is an extremely promising chemical that can be used for a variety of different purposes. However, Dashtban recognizes that furfural production from biomass has not been explored in-depth; in extraterrestrial and other harsh environments, the ability to produce and use furfural could be paramount to the success of an otherwise unsuccessful settlement. As such, Dashtban explores various methods of producing furfural with varying degrees of success, but the article ultimately concludes that more research is necessary within the field.

With the discussion of the relevant prior art attempts to provide hydrocarbon-based organisms in a usable polymer format, and to provide methods of carbon dioxide reduction in places with unusually high concentrations of carbon dioxide, the present invention involves novel methods for in-situ resource utilization, improving upon the teachings of the prior art. In particular, the present invention provides methods to increase a reactive area for photosynthetic activity and/or thermal capture/cooling, as well as a material connection between an output of an additive manufacturing system and an input to the additive manufacturing system, thereby creating an open loop system that is self-sustaining and expands as needs expand. Aspects of the methods and system will be discussed in greater detail below.

Overview of an Open-Loop System

Improving on the technologies discussed above, an aspect of the present invention includes a bioreactor produced with extrusion-based 3D printing (fused filament fabrication (FFF)) from predominantly in-situ resources ($CO_2$, and $H_2O$), with the system having the ability to scale upwards and expand to a greater area through the use of the product of the facility to make additional facilities. The bioreactor has a low initial mass and volume, and has the ability to increase a solar irradiance area over time as resources are processed into 3D filament and subsequently used to print more bioreactors. A variety of bio-based plastics are produced through a variety of production methods. The ability to fabricate additional partitioned bioreactors allows for multiple biological, chemical, and thermal production sites for target compounds used for manufacturing in a given space. The bioreactor size and number can therefore be adjusted to meet output ratios for processing and manufacturing needs.

Figure 1A:
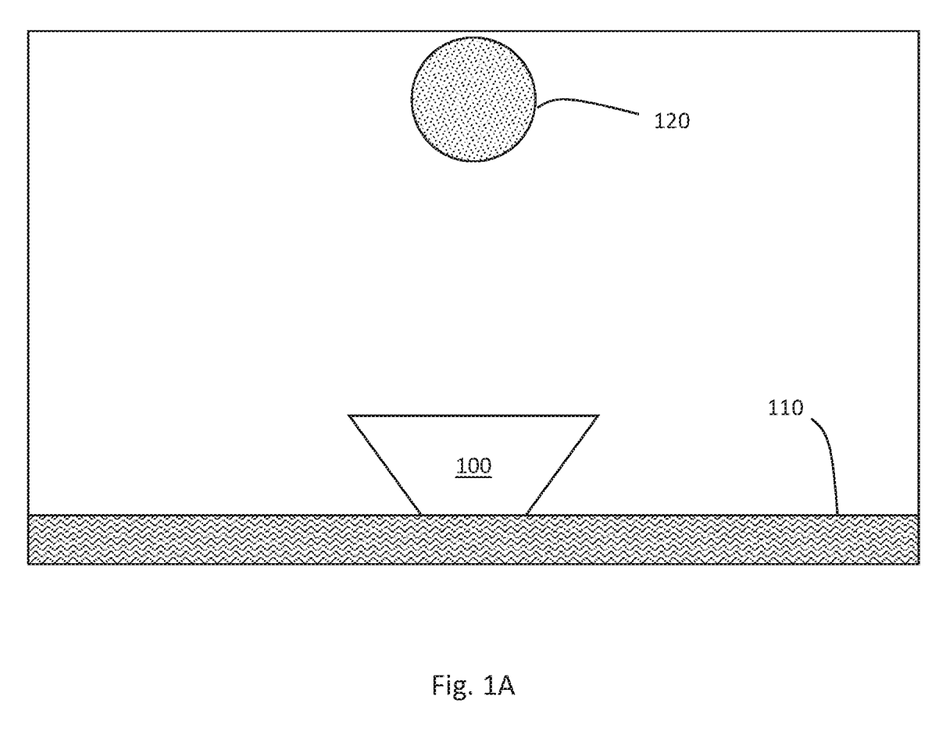
FIG. 1A is a diagram showing an inverted-trapezoidal bioreactor with the longest side of the bioreactor facing the sun.
Figure 1B:
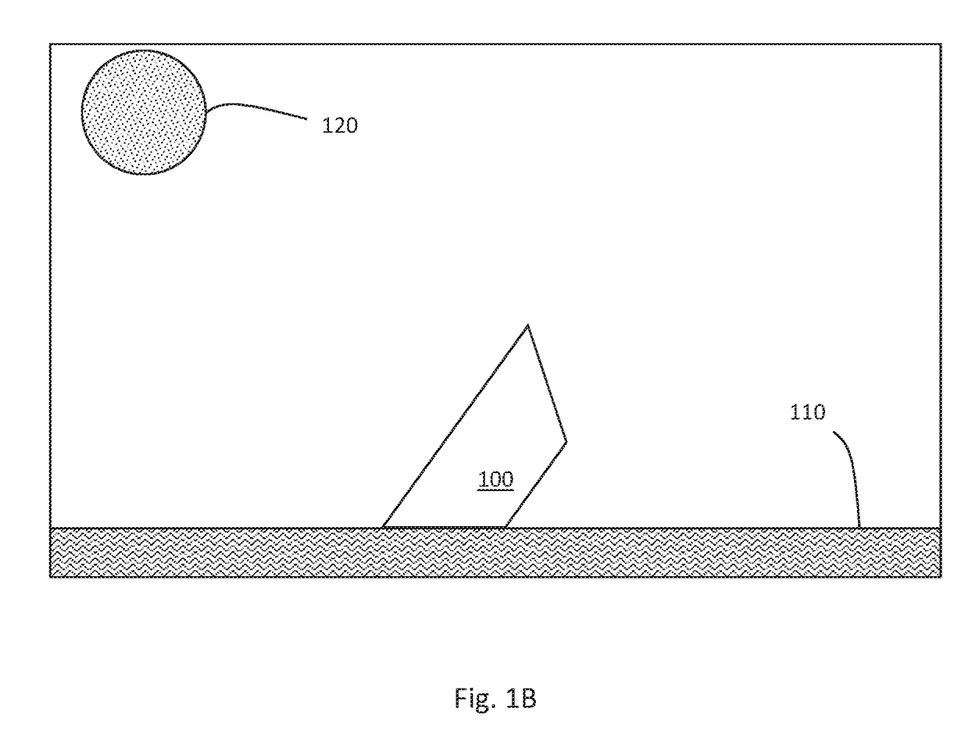
FIG. 1B is a diagram showing the inverted-trapezoidal bioreactor of FIG. 4A, showing the longest side of the bioreactor facing the sun after the bioreactor shifts in orientation.
Figure 1C:
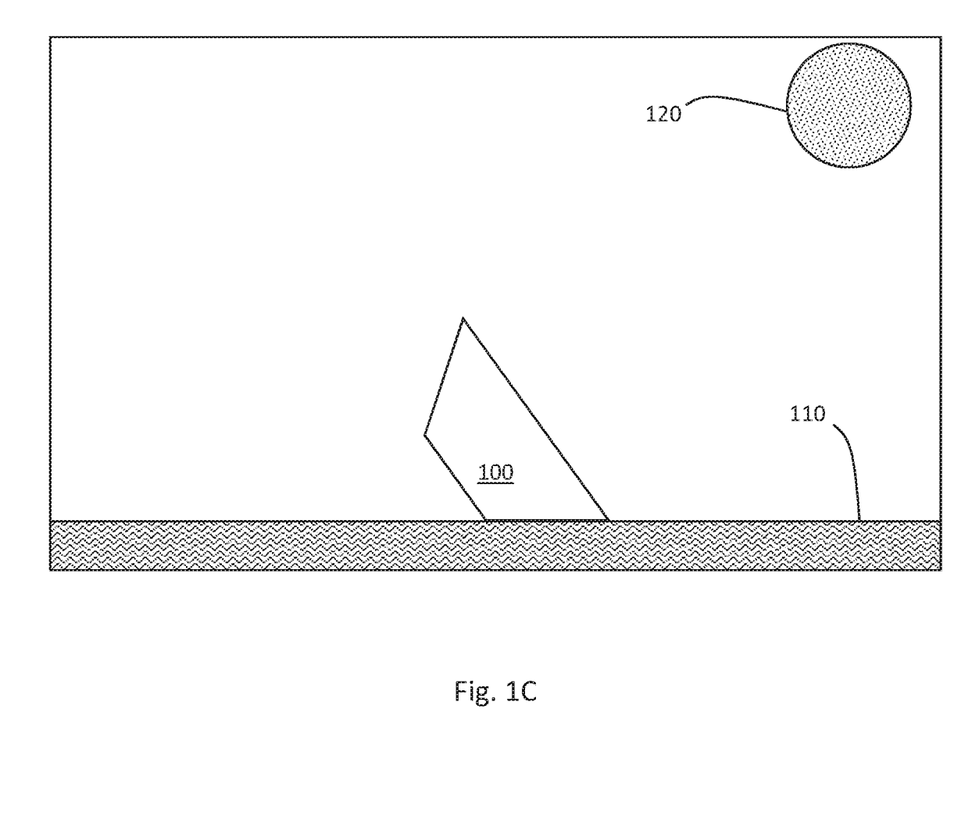
FIG. 1C is a diagram showing the inverted-trapezoidal bioreactor of FIG. 4A, showing the longest side of the bioreactor facing the sun after the bioreactor shifts in orientation.

Bioreactor/Growth Chamber in an embodiment, a bioreactor, or a growth chamber, includes design characteristics to enable the ability to scale upwards, thereby adding additional solar irradiance area. Characteristics include critical properties of porosity, light/radiation transmission as well as unique design considerations including partitioning, redundant circulation pathways, thermal distribution, solar tracking ability, internal space to pressurize to grow higher plants increasing range of options for compound production, food production, nutrient recovery, and separation. The chamber also enables rerouting of the pathway by creating a bypass, if need be. As shown in FIGS. 1A-1C, the growth chamber 100 may be trapezoidal in shape and may be oriented as an inverted trapezoid along the ground surface 110, such allows for variation in positioning for solar tracking of the sun 120 by the growth chamber, thereby increasing photosynthetic possibilities within the growth chamber. When utilized with photosynthetic organisms for feedstock, production species with high light levels productivity can be grown on plane facing the sun, while 3 other sides have organisms that thrive under lower light levels. The growth chambers can also be positioned next to each other to enable reflected light off of high light plane to be directed to adjacent chamber. As the growth chambers are modular, numerous such growth chambers can be combined in series or parallel to form larger volume and surface area facilities.

Advanced bioreactor systems may include associated hardware and software for system monitoring and control, while meeting the unique challenges of an unmanned, compact system. These will include layout, pumps, sensors, harvesting and separating biomass from solution, circulation, and aeration. Moreover, within the bioreactor, biomass may be processed into filament feedstock fed to an incorporated 3D printer, in processes that will be discussed in greater detail later in this disclosure. In addition, thermoregulation incorporating radioisotope thermoelectric generator (RTG) and photovoltaic options can provide power.

Constant thermoregulation via radioisotope or fission power systems provides constant day and night heat source to maintain adequate temperatures for biological based system. During night, when there is no sunlight on exterior of structure and temperatures decrease, aqueous biological solution can be drained from exterior shell to interior portions.

3D Printed Windmills

Following on from the previous discussion of bioreactors that can be created through the processes described throughout this specification, 3D printed windmills can also be created including biological material. If employed in an environment with wind, such as Earth or Mars, wind power can be captured by the 3D printed windmills to mechanically circulate algal or other liquid solutions about the structure and about external, coupled structures. The algae can be aerated with atmospheric $CO_2$ and pressure can be maintained through the system, thereby reducing power requirements. Examples of 3D printed windmills can be found in prior art references [14] and [15].

Hydrocarbon-Based Filament for Additive Manufacturing

Various plastic materials as feedstock for 3D printing are available and can be biosourced. Currently the preferred Biofeedstock appears to be PEF (polyethylene-2,5-furandicarboxylate), produced through various processes. Direct synthesis of plastic feedstock without using biology has been attempted and could be incorporated into the design as well. The thermal regulation of tilting chamber would be utilized.

3D printing with polyethylene-2,5-furandicarboxylate (PEF) can be performed, with PEF being made from cellulose. PEF is also clear-to-transparent, which is a useful characteristic if bio energetically sourced. A commercially available 3D printer has been used elsewhere under standard settings to successfully print objects with PEF filament. The individual layers of the printed objects were firmly bound to each other and the surface was smooth and of high quality. Tests demonstrated that the objects were resistant to dichloromethane, one of the most aggressive solvents. Due to the high thermal stability of the PEF, the printed objects could be repeatedly melted, made into filaments, and printed again. Computer calculations indicate that the individual building blocks of PEF may contain non-linear fragments and form a spiral twist, which gives an access to new types of geometry. Another important feature is a greater polarity of PEF.

Bio based Polyethylene terephthalate (PET) is another option with wide range use applications. PET is a product of terephthalic acid and ethylene glycol, and is made of 32.2 wt % monoethylene glycol (MEG) and 67.8 wt % purified terephthalic acid (PTA), combined in an esterification reactor and converted to polymer in a polycondensation reactor.

Method of Creating a Habitable Environment

Using the teachings above, a habitable environment can be created or produced by using hydrocarbon-based plastic whereas in the production from biomass hydrocarbons fixes carbon to release net oxygen from the ambient environment or various waste streams. Multiple methods of manufacturing with plastic are possible, specific methods described in the process flow diagrams of FIGS. 2-4, which will be described in greater detail below with filament 3D printing.

Figure 2:
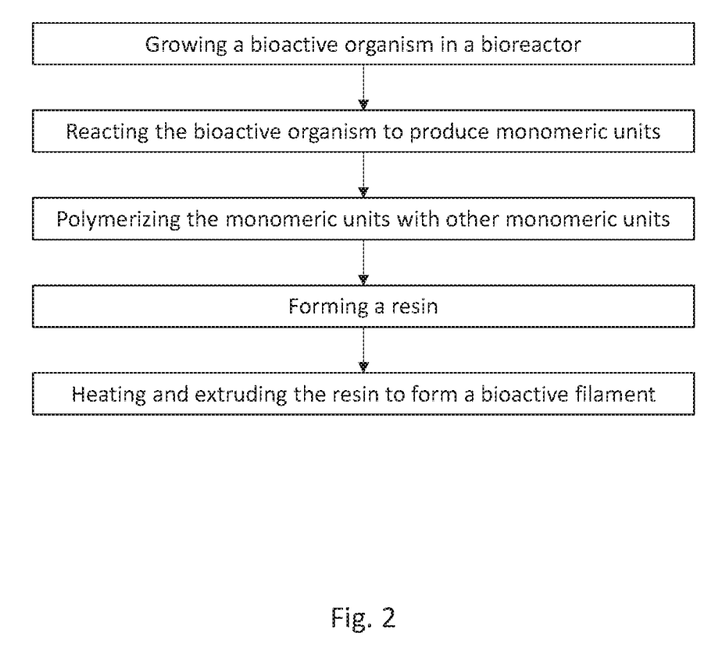
FIG. 2 is a process flow diagram describing a method of creating and extruding a hydrocarbon-based filament for use in an additive manufacturing system, the hydrocarbon-based filament capable of comprising photosynthetic structures.

As shown in FIG. 2, a general method of creating a hydrocarbon-based filament is described. The method includes the step of growing a hydrocarbon-based organism, such as algae, within a bioreactor, such as a growth chamber. Such hydrocarbon-based organisms and growth chambers are discussed in detail above. The method also includes reacting the hydrocarbon-based organisms to produce monomeric units, as is described throughout the prior art. The monomeric units can then be polymerized by reacting the monomeric units with a second group of monomeric units, creating polymers that can be formed into a resin. The method next includes the steps of heating and extruding the resin, thereby forming a hydrocarbon-based filament that can be used in additive manufacturing processes to form 3D structures capable of photosynthetic activity.

Figure 3:
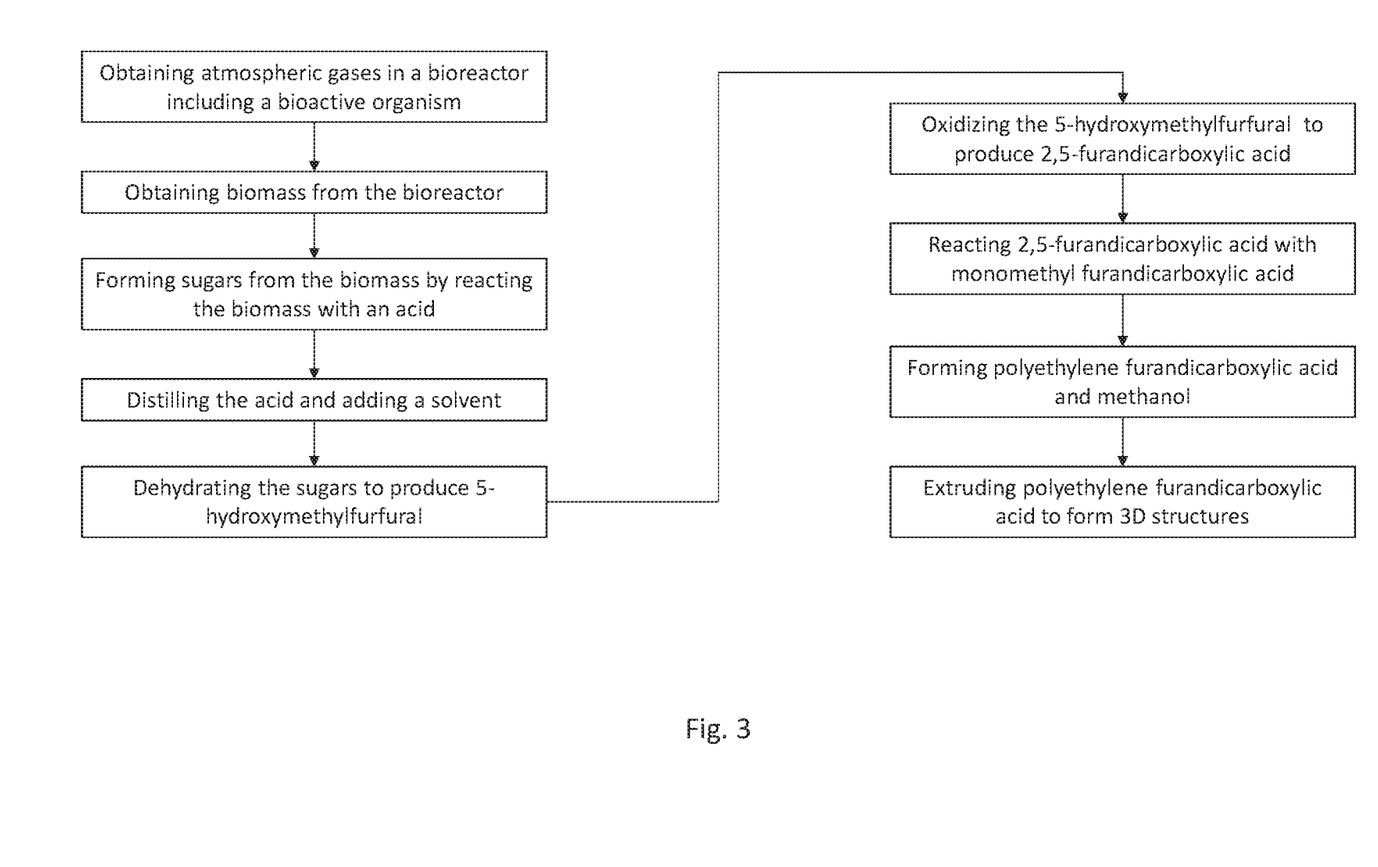
FIG. 3 is a process flow diagram describing a method of using atmospheric gases to create hydrocarbon-based filament for use in an additive manufacturing system capable of photosynthesis.

FIG. 3 expands upon the method described in FIG. 2 with more specific reactions and products shown therein. As shown in FIG. 3, the method includes capturing and obtaining atmospheric gases in a bioreactor, such as carbon dioxide. A hydrocarbon-based organism is also contained within the bioreactor, as described in FIG. 2 above. Biomass is obtained from the bioreactor, and the biomass is reacted with an acid to form pentose or hexose sugars. The acid is removed from the bioreactor via distillation, and a solvent is added to the bioreactor. The sugars are dehydrated to produce 5-hydroxymethylfurfural, which the prior art discussed above recognizes as an important chemical for sustainable life. The 5-hydroxymethylfurfural is oxidized to produce 2,5-furandicarboxylic acid, which is reacted with monomethyl ethylene glycol to form polyethylene furandicarboxylic acid and methanol. The polyethylene furandicarboxylic acid can then be extruded to form 3D structures capable of photosynthetic activity, as discussed above.

Figure 4:
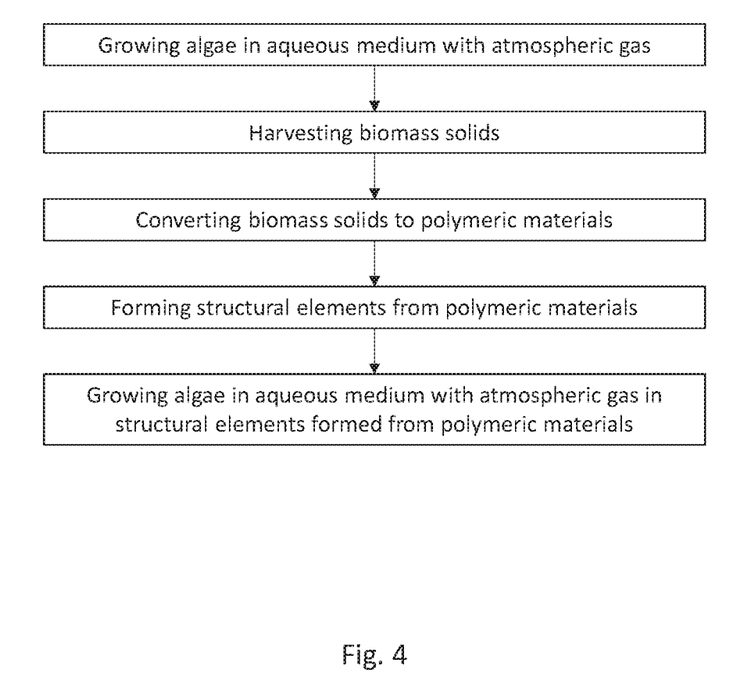
FIG. 4 is a process flow diagram describing a method of creating and harvesting hydrocarbon-based materials for use in repeating additive manufacturing systems.

FIG. 4 described yet another method of forming structural elements from hydrocarbon-based materials. The method includes the step of providing an enclosed, solar-exposed structure, such as the bioreactor discussed above. An additional step includes providing a hydrocarbon-based agent, such as algae or an algae-based substance, that is photosynthetic—this hydrocarbon-based agent may be disposed within the solar-exposed structure, or may comprise the surfaces of the solar-exposed structure. The hydrocarbon-based agent is grown within the bioreactor in an aqueous medium, together with atmospheric gas, as described in greater detail above. Biomass solids are harvested from within the bioreactor, and the biomass solids are converted into polymeric materials, or from which polymeric materials can be extracted. Structural elements are formed from the polymeric materials, with the structural elements including hydrocarbon-based materials, such as the algae discussed above. As such, the process can manufacture more hydrocarbon-based materials to be used in further reactions for further manufacturing of structural elements, and so on, thereby showing that the system can harvest hydrocarbon-based material therein to continuously produce 3D structures.

Additional Considerations

Additional examples of known bioderived resilient clear plastics can be found at references [8], [9], [10], [11], and [12].

While this specification focuses on teachings of additive manufacturing systems, it is important to consider that other fabrication methods may be used, such as injection molding, extrusion blow molder, and other methods of manufacture, so long as the materials are hydrocarbon-based, in accordance with the teachings above.

REFERENCES

[1] Kucherov, F. A. et al. "Three-Dimensional Printing with Biomass-Derived PEF for Carbon-Neutral Manufacturing." Agnew. Chem. Int. Ed. 2017, 56, 15931-15935.
[2] Murukesan, G. et al. "Pressurized Martian-Like Pure $CO_2$ Atmosphere Supports Strong Growth of Cyanobacteria, and Causes Significant Changes in their Metabolism." Orig. Life Evol. Biosph. 2015.

[3] Lingampalli, S. R. et al. "Recent Progress in the Photocatalytic Reduction of Carbon Dioxide." ACS Omega. 2017, 2, 2740-2748.

[4] Dexter, J. et al. "The state of autotrophic ethanol production in Cyanobacteria." Journal of Applied Microbiology. 2015, 119, 11-24.

[5] Gurudayal, J. B. et al. "Efficient solar-driven electrochemical $CO_2$ reduction to hydrocarbons and oxygenates." Energy Environ. Sci. 2017, 10, 2222-2230.

[6] Markou, G. et al. "Microalgal carbohydrates: an overview of the factors influencing carbohydrates production, and of main bioconversion technologies for production of biofuels." Appl. Microbiol. Biotechnol. 2012.

[7] Dashtban, M. et al. "Production of Furfural: Overview and Challenges." Journal of Science & Technology for Forest Products and Processes. 2012, 2:4, 44-53.

[8] van der Hoeven, D. "More biobased plastics for bottles: DuPont announces PTF." Bio Based Press. Feb. 2, 2016. Accessed online at the URL: haps://www.biobasedpress.eu/2016/02/more-biobased-plastics-for-bottles-dupont-announces-ptf/.

[9] DuPont. "Sustainable Plastics." Accessed online at the URL: http://www:dupont.com/products-and-services/plastics-polymers-resins/bio-based-polymers/articles/renewable-biopolymers.html.

[10] Nestle. "Danone and Nestle Waters Launch NaturALL Bottle Alliance with California Startup to Develop 100% Bio-Based Bottles. Mar. 2, 2017. Accessed online at the URL: https://www.nestleusa.com/media/pressreleases/nestle-waters-launch-alliance-naturall-bio-based-bottles.

[11] Synvina. "Publications." Accessed online at the URL: https://www.synvina.com/multimedia/publications/.

[12] Pellicori, S. "Coatings Used in Space Requirements and Solutions." Materion Coating Materials News. Accessed online at the URL: https://materion.com/media/files/advanced-materials-group/ac/ac-newsletter-article-pdfs/coatings-used-in-space_technicalpaper.pdf?1a=en&hash=14D82EF63631DC7C39D2EAD25FECDE66AD5E3BB0

[13] Gibson, M. A. et al. "Development of NASA's Small Fission Power System for Science and Human Exploration." American Institute of Aeronautics and Astronautics. Accessed online at the URL: haps://ntrs.nasa.gov/archive/nasa/casi.ntrs.nasa.gov/20140017750.pdf.

[14] Thingiverse. "Zen Windmill Powered Water Pump," Aug. 1, 2015. Accessed online at the URL: https://www.thingiverse.com/thing:950660.

[15] Holstein-Rathlou, C. et al. "Wind Turbine Power Production Under Current Martian Atmospheric Conditions." Mars Workshop on Amazonian Climate 2018. Accessed online at the URL: https://www.hou.usra.edu/meetings/amazonian2018/pdf/4004.pdf.

[16] Raymond M. Wheeler "Agriculture for Space: People and Places Paving the Way" Open Agriculture. 2017; 2: 14-32 Accessed online at the URL: http://sciences.ucf.edu/class/wpcontent/uploads/sites/58/2017/02/Wheeler_AgricultureForSpace_People-Places_OpenAgriculture_2017, pdf.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of manufacturing a habitable hydrocarbon-based three-dimensional structure, the method comprising the steps of:
    removing atmospheric gases into a bioreactor disposed within an ambient environment in communication with an atmosphere containing the atmospheric gases;
    reacting the removed atmospheric gases with an aqueous mixture including a hydrocarbon-based organism to form a solid biomass;
    digesting the solid biomass with a solution of α-hydroxysulfonic acid to form sugars selected from the group consisting of pentose sugars, hexose sugars, and mixtures thereof;
    dehydrating the sugars to produce 5-hydroxymethylfurfural;
    oxidizing the 5-hydroxymethylfurfural to produce 2,5-furandicarboxylic acid;
    reacting the 2,5-furandicarboxylic acid with monomethyl ethyleneglycol to form poly ethylene furandicarboxylic acid and methanol; and
    extruding the polyethylenefurandicarboxylic acid to form a three-dimensional structure.

2. The method of claim 1, wherein the atmospheric gases include at least 10% $CO_2$ and less than 3% $O_2$.

3. The method of claim 2, wherein the removal of atmospheric gases reduces the concentration of $CO_2$ in the ambient environment, and wherein the reaction in the bioreactor increases the concentration of $O_2$ in the ambient environment.

4. The method of claim 1, wherein the hydrocarbon-based organism is algae.

5. The method of claim 1, wherein the biological reactor is operated at a pressure approximately equal to a pressure of the ambient environment surrounding the bioreactor.

6. The method of claim 1, wherein the three-dimensional structure is selected from the group consisting of translucent films, plates, sheets, panels, other planar structures, and combinations thereof.

7. The method of claim 1, wherein the three-dimensional structure is an inverted-trapezoidal shape, wherein the shorter of the pair of parallel base surfaces of the inverted-trapezoidal shape is disposed on a ground surface in a first configuration.

8. The method of claim 7, further comprising a step of rotating the inverted-trapezoidal three-dimensional structure to a second configuration, in which one of the tapered sides of the inverted-trapezoidal shape is disposed on the ground surface.

9. The method of claim 8, further comprising a step of rotating the inverted-trapezoidal three-dimensional structure to a third configuration, in which the other of the tapered sides of the inverted-trapezoidal shape is disposed on the ground surface.

10. The method of claim 1, further comprising a step of increasing an area disposed within the bioreactor by securing the formed three-dimensional structure to the bioreactor, thereby increasing the habitable area within the bioreactor.

* * * * *